United States Patent [19]

Shackelford

[11] 4,240,429
[45] Dec. 23, 1980

[54] NEEDLE INJECTION DEVICE FOR DELIVERING FLUID

[75] Inventor: Carl L. Shackelford, San Pablo, Calif.

[73] Assignee: Altex Scientific, Inc., Berkeley, Calif.

[21] Appl. No.: 48,441

[22] Filed: Jun. 14, 1979

[51] Int. Cl.³ .............................................. A61M 5/00
[52] U.S. Cl. .............................. 128/218 NV; 128/216
[58] Field of Search ....... 128/218 R, 218 N, 218 NV, 128/215, 216, 247, 221

[56] References Cited

U.S. PATENT DOCUMENTS

| 3,380,448 | 4/1968 | Sadove et al. | 128/215 |
| 3,603,471 | 9/1971 | Harris, Sr. et al. | 128/218 NV X |
| 4,096,860 | 6/1978 | McLaughlin | 128/221 X |

FOREIGN PATENT DOCUMENTS 1593629  7/1970  France ................. 128/218 N

Primary Examiner—John D. Yasko
Attorney, Agent, or Firm—Bielen and Peterson

[57] ABSTRACT

A needle injection device for delivering fluid through an opening in a body utilizing a pair of bushings placed substantially in end-to-end orientation. A filter is placed adjacent one of the bushings generally within the opening. The bushing nearest the filter is constructed of sealing material such that forcing of the first bushing against the second bushing seals the area between the needle and the sides of the opening immediately above the filter.

10 Claims, 4 Drawing Figures

NEEDLE INJECTION DEVICE FOR DELIVERING FLUID

BACKGROUND OF THE INVENTION

The present invention relates to a novel device for utilizing a hypodermic needle for injecting substances into a body such as a high pressure sample injection valve found on a liquid chromatography system.

The injection of known quantities of unknown solutions into liquid chromatography systems is imperative for proper and accurate analysis of the same. Prior methods and apparatuses associated with injecting liquid samples have failed because of leakage. Also, prior methods of injecting liquid samples have proved inconvenient or unworkable in many cases. Such prior devices use a variety of clamps and seals which are difficult to manipulate with the delicacy required in the liquid chromatography field. Moreover, the use of a needle or cannula often produces wear particles which eventually clog the liquid chromatography valves or other parts of the system.

There is a need for a simple, efficient, and non-contaminating sample injection device which is compatible with a conventionally produced hypodermic needle and syringe.

SUMMARY OF THE INVENTION

In accordance with the present invention a novel needle injection device for delivering fluid to an opening in a body such as a liquid chromatography valve is provided.

The device of the present invention employs the conventional recessed threaded fitting found on most liquid chromatography valves. It has been the practice in recent years to employ a hypodermic needle and syringe to accurately meter amounts of sample being analyzed in the liquid chromatography system.

The device of the present invention employs a first bushing which is adapted for substantially surrounding at least a portion of the needle. The first bushing includes a first and second end portion. A second bushing which is also adapted for substantially surrounding at least a portion of the needle is placed in abutting configuration with the first bushing. The second bushing also includes a first and second end portion and is oriented such that its second end portion is adjacent the first end portion of the first bushing. The second bushing is constructed of sealing material, being basically flowable or deformable upon the application of pressure thereon.

Means for filtering the fluid intended for passage through the opening is also included in the present device. Such filtering means would be located through the opening of the body and adjacent the first end portion of the second bushing.

The present device may additionally comprise means for guiding the needle into the first bushing. Such guiding means may take the form of a cap which would partially extend within the bore of the first bushing. To prevent damage to the needle and guiding means would be constructed of softer material than the needle itself.

The device of the present invention may also take the form in which the first bushing is split into first and second hollow members with spring means therebetween for urging the first and second members apart. The first hollow member may position within the second hollow member with each of the hollow members having first and second end portions. The hollow members may be oriented such that the first end portion of the first hollow member is adjacent the second end portion of the second bushing. Also, the second end portion of the first hollow member may be placed adjacent the first end portion of the second hollow member. The spring means would be placed in abutment in relation to the second end portion of the first hollow member and the second end portion of the first hollow member. In effect, the first hollow member would slide within the bore of the second hollow member and exert a pressure on the second bushing which would be predetermined and dependant upon the strength of the spring means.

In one aspect of the present invention the means for forcing the first end portion of the first bushing into contact with the second end portion of the second bushing may take the form of a threaded portion on the exterior of the second hollow member. Such threaded portion would threadingly engage a threaded portion on the side portions of the opening of the body. Thus, the device may be screwed into place and sealed in the same motion. The device may also include means for stopping the movement of the first bushing toward the second bushing i.e. an attenuation of the means for forcing said first end portion of the first bushing into contact with the second end portion of the second bushing. Such stop means may take the form of a shoulder or flat end portion on the first bushing which would engage a part of the body which surrounds the opening therewithin.

It may be apparent that a novel and useful needle injection device for delivering fluid through an opening in a body has been described.

It is therefore an object of the present invention to provide a needle injection device for delivering fluid through an opening in a body which prevents blockage in a high pressure valve found in a liquid chromatography system rendering such a valve inoperative.

It is another object of the present invention to provide a needle injection device which provides filtering means for preventing wear particles from entering the liquid chromatography system and is removable for replacement or to prevent absorbtion of the solution being analyzed.

Yet another object of the present invention is to provide a needle injection device for delivering fluid through an opening in a body which includes filtering means that can be cleaned by flushing or back-flushing while in place.

Another object of the present invention is to provide a needle injection device for delivering fluid through an opening in a body which provides a simplified method for sealing space around the needle or cannulae employed for depositing a sample solute.

Still another object of the present invention is to provide a needle injection device for delivering the fluid through an opening in a body which eliminates human error and is compatible with injection techniques in the field of the invention.

The invention possesses other objects and advantages especially as concerns particular features and characteristics thereof, which will become apparent as the specification continues.

For a better understanding of the invention, reference is made to the following detailed description.

DESCRIPTION OF THE PREFERRED EMBODIMENT

Various aspects of the present invention will evolve from the following detailed description of the preferred embodiments thereof, which should be taken in conjunction with the heretofore described drawings.

Figure 1:
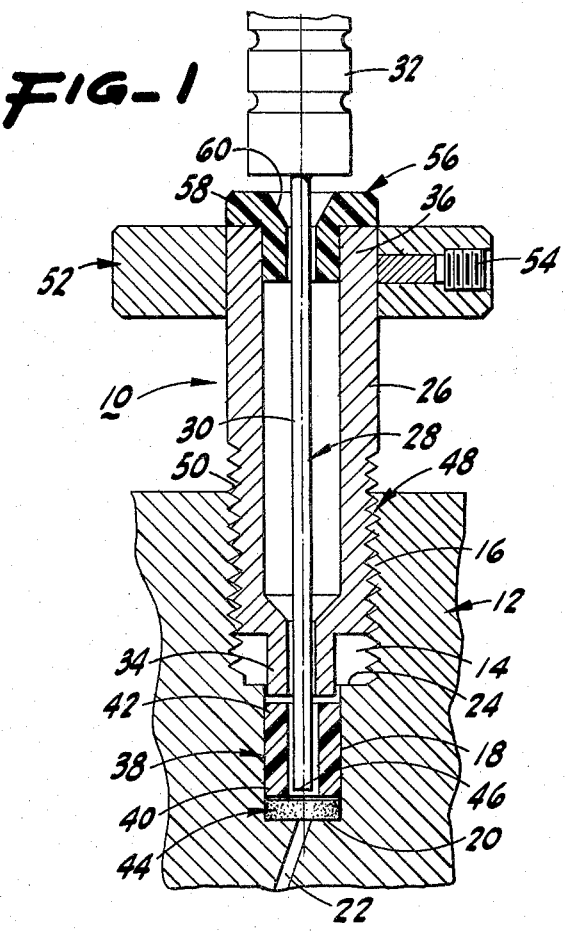
FIG. 1 is a sectional view of an embodiment of the device.

With reference to FIG. 1 the apparatus as a whole is depicted by reference character 10. The device of the present invention is used in conjunction with a body 12 having an opening 14. Opening 14 includes threaded side portion 16 as well an unthreaded side portion 18 and bottom 20, FIG. 1. Passageway 22 leads to a liquid chromatography system, specifically the injection loop of a high pressure liquid chromatography valve adapted for injection of samples. Shelf 24 marks the transition between threaded side portion 16 and unthreaded side portion 18. Opening 14 within body 12 is typical of sample injection ports associated with liquid chromatography systems and is, in that respect, known in the art.

Device 10 includes as one of its elements a bushing 26 which substantially surrounds at least a portion of hypodermic needle 28, consisting of cannulae 30 and hub 32. First bushing 26 includes a first end portion 34 and a second end portion 36. First bushing 26 may be constructed of any rigid or semirigid material which is nonreactive to the substances intended for transfer from the inside of hypodermic needle 28 to passageway 22. It should be noted, that a metered syringe usually attaches to the upper portion of hub 32 of hypodermic needle 28.

A second bushing 38 also substantially surrounds at least a portion of needle 28, more precisely cannulae 30, within opening 14. Second bushing 38 includes a first end portion and a second end portion 42. First end portion 34 of first bushing 26 lies adjacent second end portion 42 of second bushing 38 generally within opening 14. Second bushing 38 is constructed of sealing material such as Teflon, neoprene, and the like which are deformable under the application of pressure.

The embodiments shown in FIGS. 1 through 4 depict first bushing 38 as being within opening 14 along unthreaded side portion 18 of body 12 and the first bushing 26 as lying against side portion 16 of body 12. The significance of the interaction between first bushing 26 and second bushing 38 will be described hereinafter.

The device 10 also embraces means 44 for filtering any fluid intended for passage through opening 14 via the bore of hypodermic needle 28 and into passageway 22. Means 44 may take the form of a disc shaped object constructed of sintered metal. For example, filtering means 44 may possess a volume of two microliters with thirty percent of that volume considered as open. The filtering means 44 is able to withstand substantial pressure without any deleterious effects on its filtering capabilities. Filtering means 44 removes wear particles inherent in the coupling and/or decoupling of device 10 with body 12. Such wear particles of metal, plastic, and other materials cause wear on any valve mechanisms connected directly or indirectly to passageway 22.

Also, solvents and samples employed during liquid chromatography analyses are "dirty". Often the plunger of microbore syringes used in conjunction with hypodermic needle 28 are rapidly moved up and down within the syringe barrel to remove air bubbles. Such action often exfoliates glass, metal, and other particles which foul the system proper. Moreover, syringe 28 includes a square tip 46 which tends to scrape particles from device 10 during operation of the same. Filter means 44 in the form of the sintered metal frit is removable which is useful in the processing of pure small volume samples where no absorbtion of sample is permitted. It should be pointed out that frit 44 may be flushed or back-flushed by a clean mobile phase between analyses.

Device 10 further includes means 48 for forcing first end portion 34 of first bushing 26 into contact with second end portion 42 of second bushing 38. Forcing means 48 also causes contact between first end portion 40 of second bushing 38 and filtering means 44. The result of the action of forcing means 48 will be described hereinafter. Forcing means 48 is depicted in the embodiment as a threaded fitting comprising a threaded portion 50 of first bushing 26 which threadingly engages threaded side portion 16 of body 12. A knob 52, which may have knurled surface portions aids in the turning of first bushing 26. Screw 54 holds knob 52 to the exterior of first bushing 26. Knob 52 may be constructed of any rigid material such as stainless steel, aluminum, and the like. Other embodiments may be employed as means 48 for forcing contact of first bushing 26 with second bushing 38, but it has been found that threaded fittings are the most convenient.

In addition, device 10 may also include means 56 for guiding needle 28 into the bore of first bushing 26. As shown guiding means 56 may take the form of a cap 58 which snuggly fits over the upper end of first bushing 26 and extends to the interior of the same. Cap 58 includes a beveled portion which minimizes the generation of wear particle heretofore discussed. Guiding means 56 may be constructed of a material softer in relation to hypodermic needle 28 such as Teflon, Kel-f, and the like.

Figure 2:
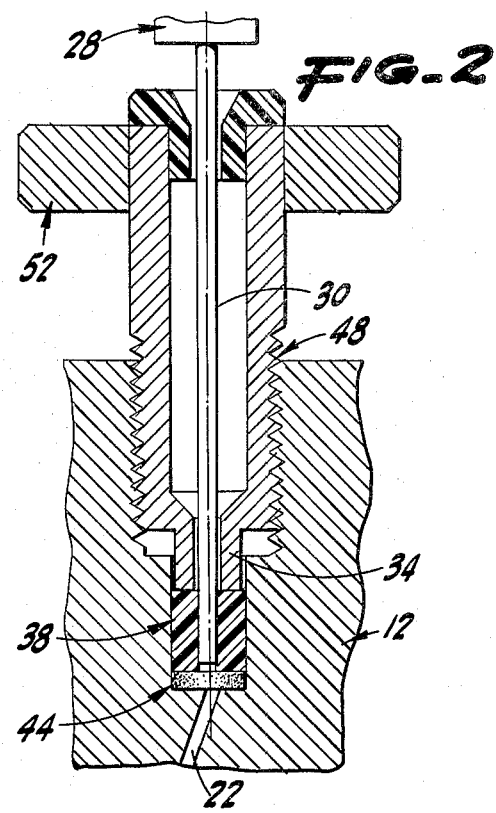
FIG. 2 is a sectional view of an embodiment of the device shown in FIG. 1 in a tightened condition.

Turning to FIG. 2, knob 52 and connected first bushing 26 have been turned such that forcing means 48 has been activated and pressure has been exerted on second bushing 38 by first bushing 26. First bushing 38 has deformed or cold flowed to seal the exterior of hypodermic needle 28 and the side portion 18 of body 12 at this point fluid flowing through hypodermic needle 28 would pass through filter means 44 and into passageway 22. It has been found that a very good seal results when at least four ounces of force is required to remove the needle from the bore of second bushing 38.

Figure 3:
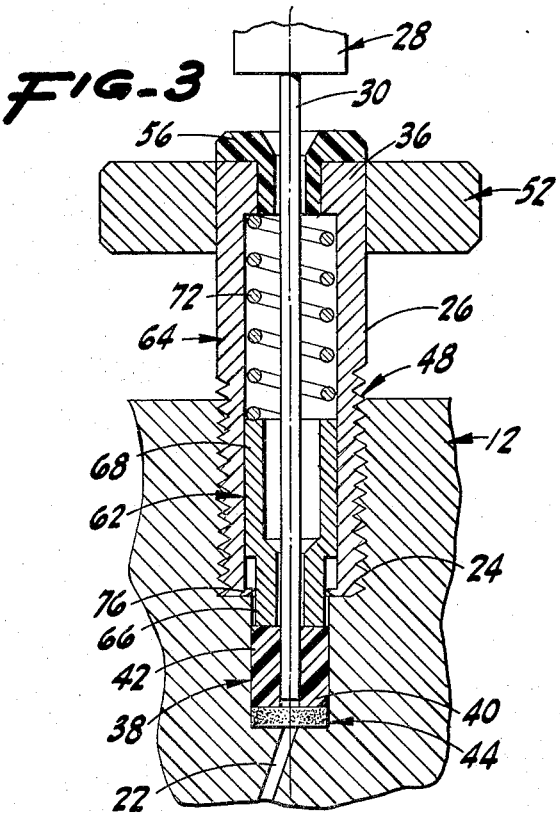
FIG. 3 is a sectional view of another embodiment of the device in a tightened position.

As an alternate embodiment, FIG. 3 depicts device 10 where first bushing 26 has been formed into a first hollow member 62 which slides within the bore of a second hollow member 64. First hollow member 62 has a first end portion 66 and a second end portion 68 as depicted in FIG. 3, the first end portion 66 of first hollow member 62 lies adjacent second end portion 42 of second bushing 38. This embodiment of device 10 includes spring means 70 which urges apart first and second hollow members 62 and 64. Specifically, the present embodiment illustrates a structure where second end portion 68 of first hollow member 62 and second end portion 36 of first bushing 26 contact either end of spring means 70 which has taken the form of a coil spring 72. Spring means 70 surrounds the cannulae 30 of hypodermic needle 28.

Figure 4:
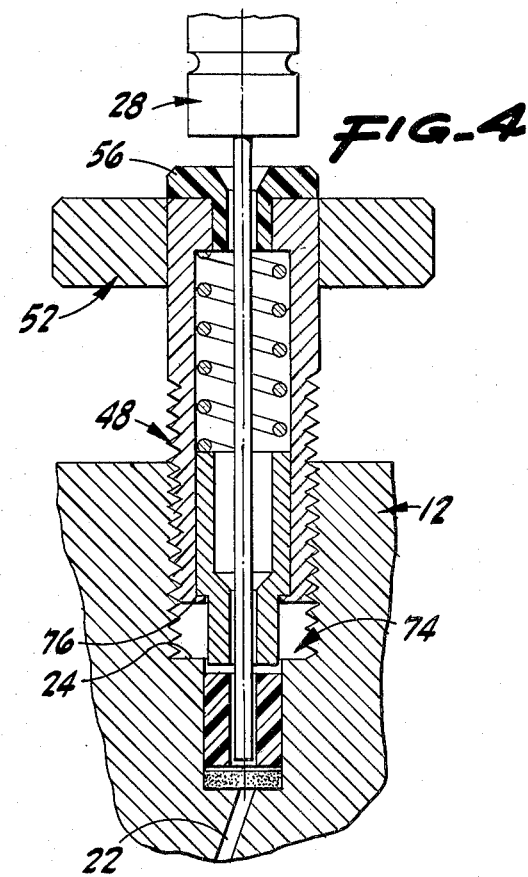
FIG. 4 is a sectional view of the embodiment of the device depicted in FIG. 3.

FIG. 4 shows the immediately above described embodiment before activation of means 48 for forcing first and second bushings 26 and 38 together. The device also includes means for stopping or attenuating movement of first bushing 26 toward second bushing 38 caused by forcing means 48. Such stopping means includes providing first bushing 26 with a shoulder 76 which is adapted for engagement with a portion of body 12 surrounding opening 14, eg: shelf 24. It should be noted that the embodiment depicted in FIGS. 3 and 4 include many elements heretofore described with the embodiment shown in FIGS. 1 and 2. eg: filtering means 44, guiding means 56, gripping knob 52, and the like which will not be reiterated for the sake of brevity. Stopping means 74 permits the operator of device 10 to merely screw in the first hollow member 62 of first bushing 26 to the point of stoppage. Spring means 70 is sized to exert the proper force on second bushing 38 and create the seal hereinbefore described. FIG. 3 depicts essentially the same seal as the seal shown in FIG. 2. Thus, an element of human error (over tightening or under tightening) is eliminated by this construction.

In operation the user of the embodiment shown in FIGS. 1 and 2 drops filtering means 44, and the second bushing 38 within the unthreaded portion of opening 14 of body 12. Second bushing 26 is threaded along side the side portion 16 of body 12 to the point of engagement between first bushing 26 and second bushing 38. Hypodermic needle 28 is inserted through the first bushing 26 and second bushing 38 with or without the employment of guiding means 56. Knob 52 is turned such that forcing means 48 comes into play such that second bushing cold flows and creates a seal around hypodermic needle cannulae 30. The user then presses the plunger of the syringe (not shown) and forces the sample through cannulae 28, filter means 44, and into passageway 22. In a liquid chromatography system the sample is then analyzed thereby.

In the embodiment shown in FIGS. 3 and 4 the operator places filtering means 44 and second bushing 38 within opening 14 of body 12 as before. Second bushing 26 including first and second hollow members 62 and 64 are placed on top of bushing 38 by engagement of the threaded outer portion 50 of first bushing 26 and the female threaded side portion 16 of body 12. The hypodermic needle cannulae 30 is inserted through first and second bushings 26 and 38 such that square tip 46 is in the vicinity of filtering means 44 or touches the same. Knob 52 is turned such that stop means 74 operates, at which point second bushing 38 seals the area surrounding cannulae 30 as before. Spring means 70 will exert the proper pressure on second hollow member 64 to allow the heretofore described seal to effectively work.

While in the foregoing specification embodiments of the invention have been set forth in considerable detail for the purposes of making a complete disclosure of the invention, it will be apparent to those of ordinary skill in the art that numerous changes may be made in such details without departing from the spirit and principles of the invention.

What is claimed is:

1. A needle injection device for delivering fluid through an opening in a body comprising:

a. a first bushing adapted for substantially surrounding at least a portion of the needle, said first bushing having first and second end portions;
    b. a second bushing adapted for substantially surrounding at least a portion of the needle, said second bushing having a first end portion and a second end portion, said first end portion of said first bushing being adjacent said second end portion of said second bushing, said second bushing adapted for being at least partially within the opening in the body and being constructed of sealing material;
    c. means for filtering the fluid intended for passage through the opening, said filtering means being adjacent said first end portion of said second bushing;
    d. means for forcing said first end portion of said first bushing into contact with said second end portion of said second bushing and for forcing said first end portion of said second bushing into contact with said filtering means such that said second bushing seals the exterior of the needle and the sides of the opening.

2. The needle injection device of claim 1 which additionally comprises means adapted for guiding the needle into said first bushing, said guiding means being adapted for at least partially surrounding the needle.

3. The needle injection device of claim 2 in which said guiding means is constructed of material softer than the needle and includes a portion which positions within said second end portion of said first bushing.

4. The needle injection device of claim 1 in which said first bushing includes a first hollow member and a second hollow member, and spring means for urging apart said first and second hollow members.

5. The needle injection device of claim 4 in which at least a portion of said first hollow member positions within said second hollow member, said first hollow member including a first end portion and a second end portion, said first end portion of said first hollow member being adjacent said second end portion of said second bushing and said second end portion of said first hollow member being adjacent said spring means.

6. The needle injection device of claim 5 in which said spring means comprises a spring abutting said second end portion of said first hollow member and said second end portion of said first member, said spring being substantially confined to the hollow portion of said second hollow member.

7. The needle injection device of claim 5 in which said means for forcing said first end portion of said first bushing into contact with said second end portion of said second bushing comprises a threaded portion on the exterior of said second hollow member adapted for threadingly engaging a threaded portion on the side portions of the opening in the body.

8. The needle injection device of claim 5 in which additionally comprises means for stopping movement of said first bushing toward said second bushing.

9. The needle injection device of claim 7 in which said stop means comprises providing said first end portion of said first bushing with a shoulder adapted for engagement with a portion of body surrounding the opening.

10. The needle injection device of claim 9 which additionally comprises means adapted for guiding the needle into said first bushing, said guiding means being adapted for at least partially surrounding the needle.

* * * * *